(12) United States Patent
Yang

(10) Patent No.: US 6,179,613 B1
(45) Date of Patent: Jan. 30, 2001

(54) COMPRESSED WATER SUPPLY SYSTEM AND SUPPLY DEVICE FOR DENTAL UNIT-CHAIR

(76) Inventor: Won Dong Yang, 102-403 International Mountain Villa APT Shillim 10 dong, Kwanak-ku, Seoul (KR)

( * ) Notice: Under 35 U.S.C. 154(b), the term of this patent shall be extended for 0 days.

(21) Appl. No.: 09/277,782

(22) Filed: Mar. 29, 1999

(30) Foreign Application Priority Data

Apr. 9, 1998 (KR) .................................................. 98-5867
Sep. 26, 1998 (KR) ................................................ 98-40085

(51) Int. Cl.[7] ................................................ A61G 17/02
(52) U.S. Cl. .............................................. 433/80; 433/82
(58) Field of Search ................................ 433/80, 82, 84, 433/88

(56) References Cited

U.S. PATENT DOCUMENTS

| 4,699,589 | * | 10/1987 | Friedman et al. | 433/80 |
|---|---|---|---|---|
| 4,770,632 | * | 9/1988 | Ryder et al. | 433/80 |
| 4,793,807 | * | 12/1988 | Friedman et al. | 433/80 |
| 5,004,535 | * | 4/1991 | Bosko et al. | 210/90 |
| 5,295,829 | * | 3/1994 | Frey et al. | 433/80 |
| 5,360,338 | * | 11/1994 | Waggoner | 433/80 |
| 5,567,311 | * | 10/1996 | Jang | 210/243 |
| 5,709,546 | * | 1/1998 | Waggoner | 433/82 |
| 5,824,215 | * | 10/1998 | Suh | 210/249 |
| 5,837,204 | * | 11/1998 | Prevost et al. | 433/80 |
| 5,942,125 | * | 8/1999 | Engelhard et al. | 433/82 |
| 5,947,727 | * | 9/1999 | Kimura et al. | 433/80 |

\* cited by examiner

*Primary Examiner*—Ralph A. Lewis
(74) *Attorney, Agent, or Firm*—Ladas and Parry

(57) ABSTRACT

A pressurized water supply system for a dental unit-chair comprising a water purifier purifying or sterilizing water from a water supply source, and supplying the water to which a given pressure is applied to a medical instrument instrument. A pressurized water supply device for a dental unit-chair includes a case, an inflow tube provided to the case and connected to a water supply source, a pump installed within the case and connected to the inflow tube to jet out the water from the water supply source under a given pressure, a water purifier provided to the case in multi-stage and removing various alien substances, chemical substances, heavy metals, ions, germs, etc. from the water supplied from the pump, and A pressurized water supply tube provided to the case, connected with the water purifier, and connected to a medical instrument installed on the dental unit-chair, thus providing the compressed water thereto.

8 Claims, 4 Drawing Sheets

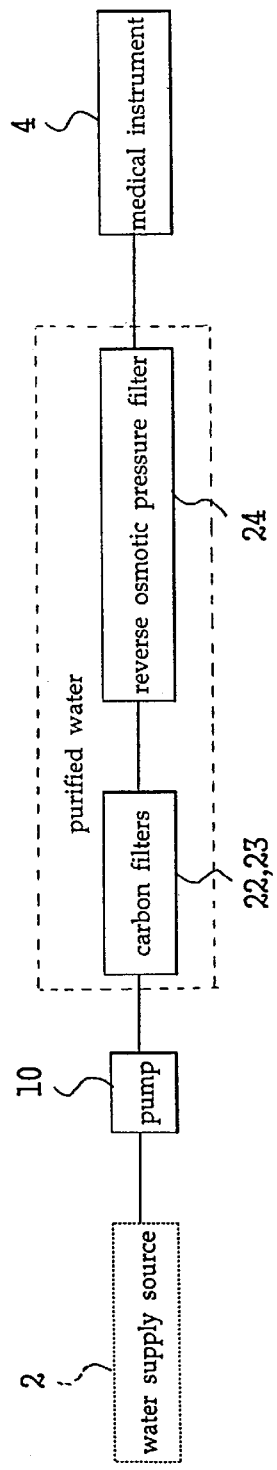
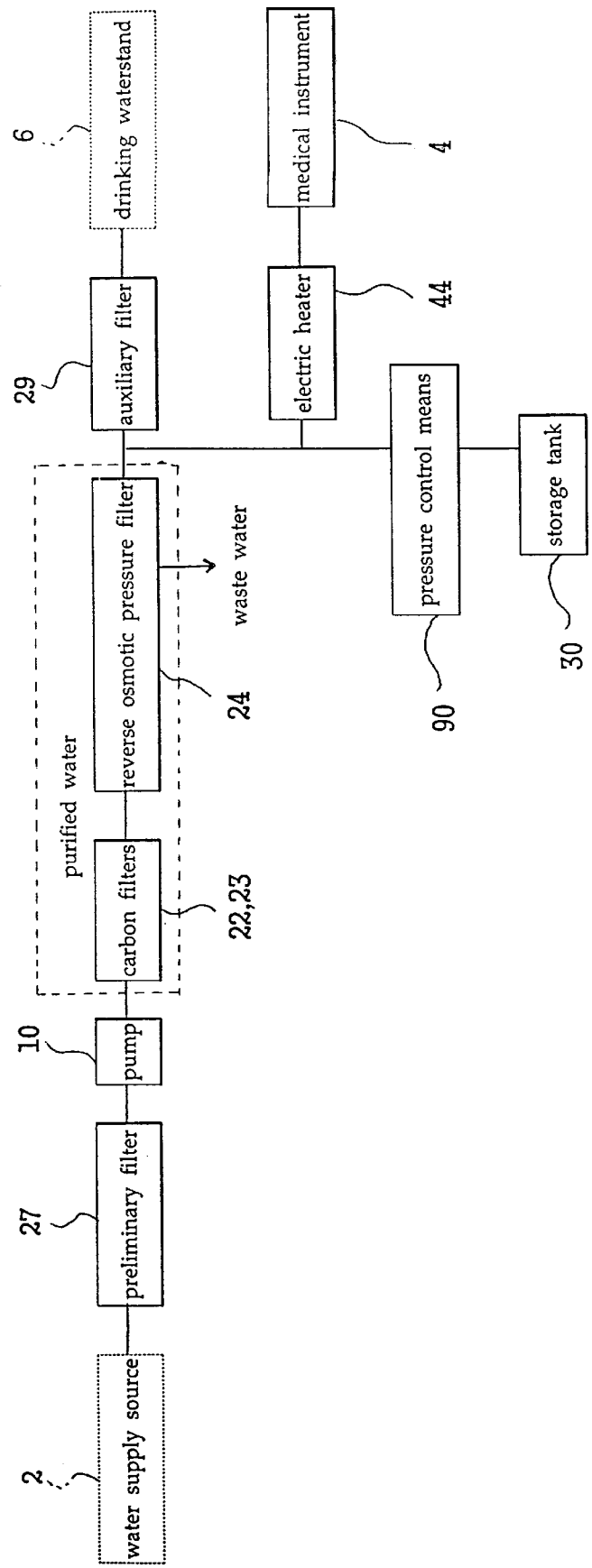

[FIG. 3]
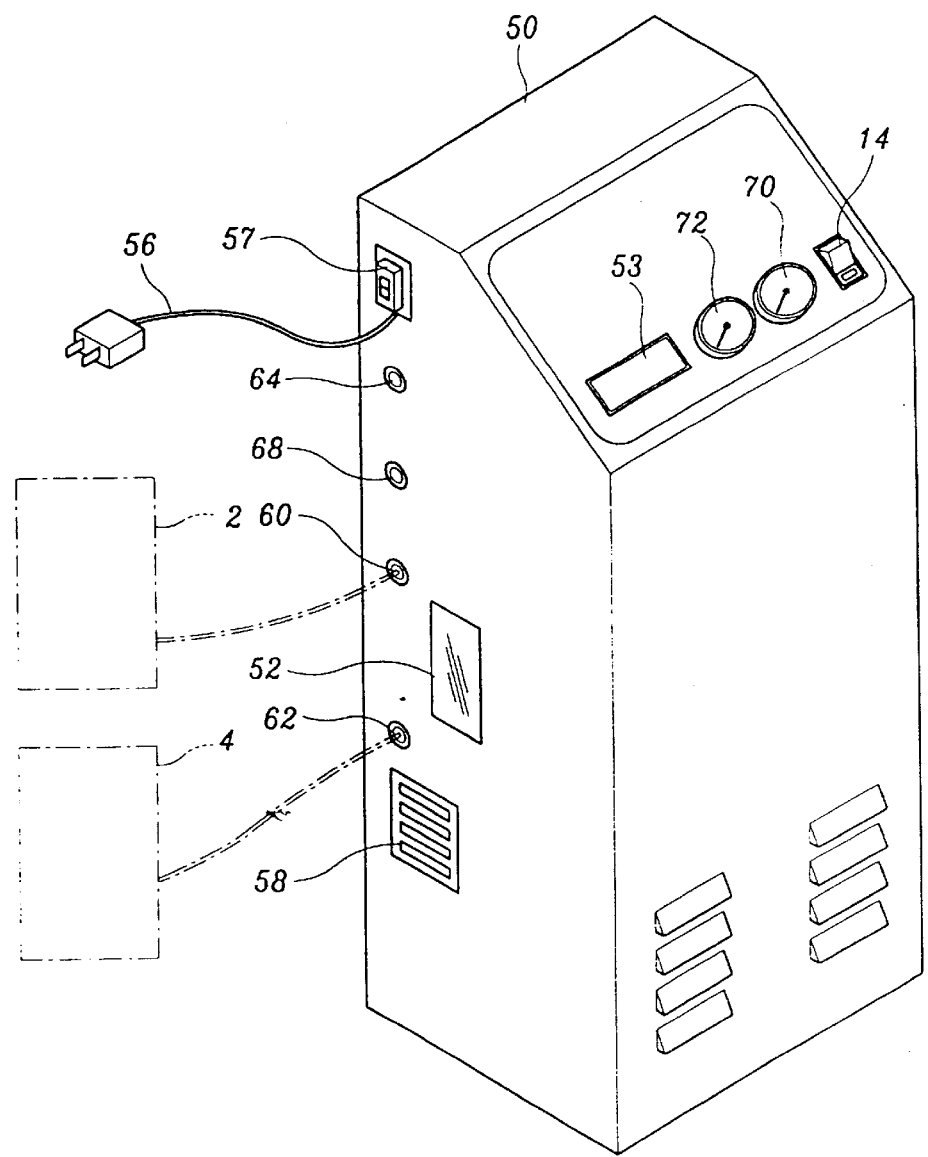

[FIG. 4]
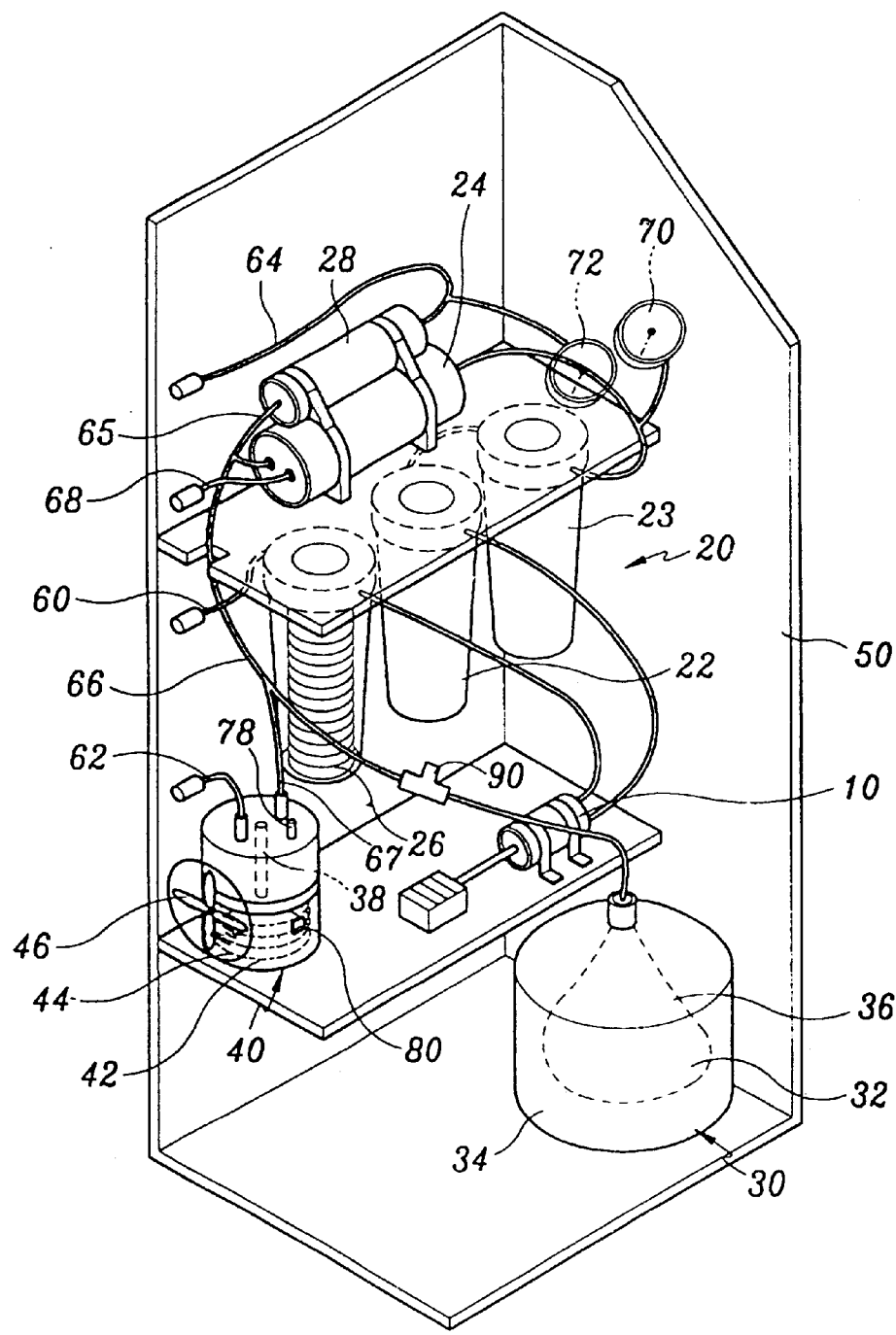

[FIG. 5]
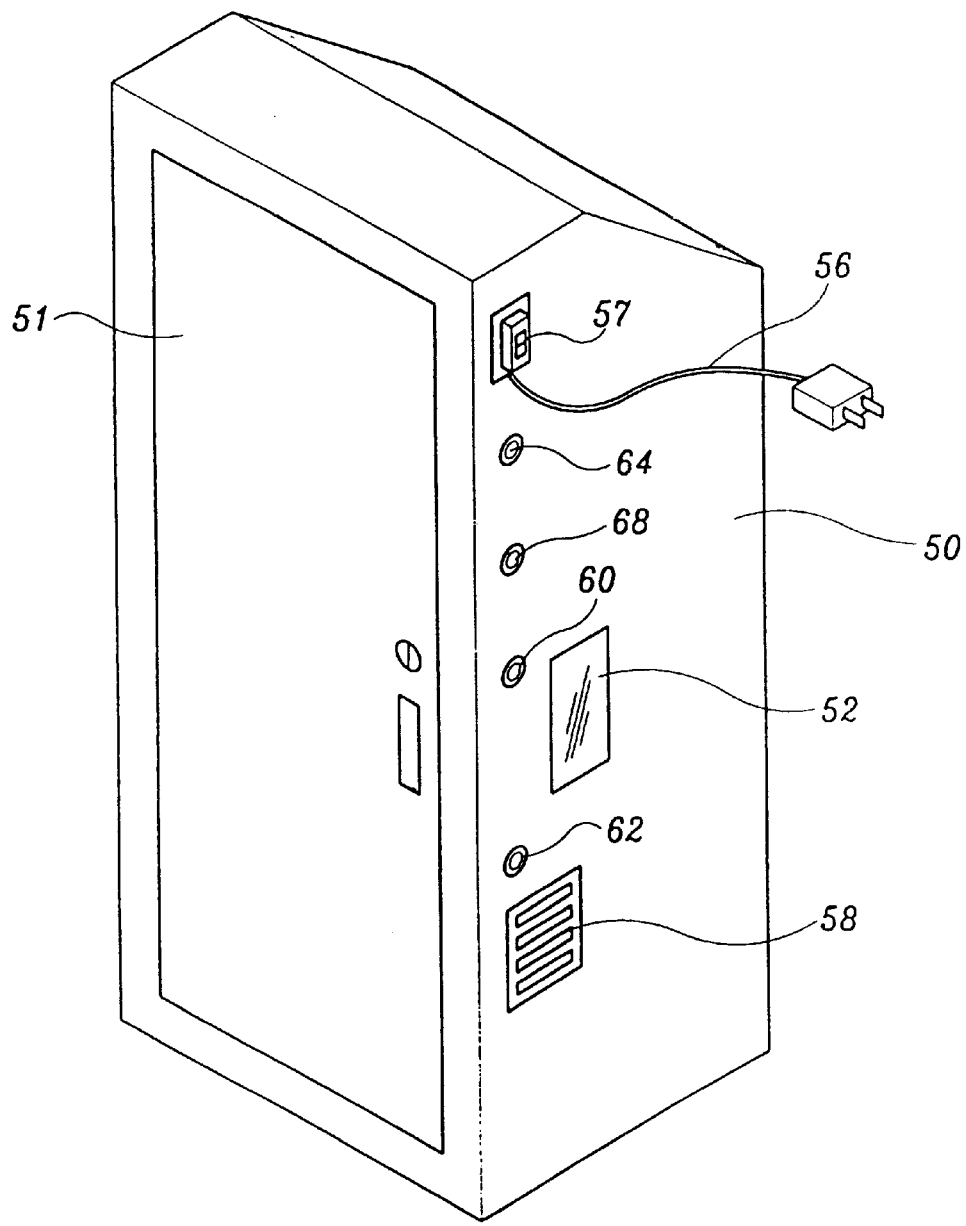

COMPRESSED WATER SUPPLY SYSTEM AND SUPPLY DEVICE FOR DENTAL UNIT-CHAIR

BACKGROUND OF THE INVENTION

1. Field of the Invention

The present invention relates to a compressed water supply system and a supply device for a dental unit-chair. More particularly, it relates to a compressed water supply system and a compressed water supply device for a dental unit-chair which is capable of purifying and providing continuously the purified and compressed water to a medical instrument installed on the dental unit-chair, maintaining a given level of pressure.

2. Discussion of Related Art

In case that a high speed rotation or pressure jet is required in medical instruments such as dental unit-chairs, the compressed air supplied from an air compressor is used. A contra-angle handpiece of dental surgery rotates a finishing bur at high speed (about several thousands or several ten thousands revolutions per minute) by using the compressed air, and a three-way syringe jets out the compressed air and the compressed water to clean a required portion of a human body.

The above contra-angle handpiece uses the compressed water of the same pressure level to cool the friction heat, generated from the finishing bur rotating at high speed, and to remove remainders. This contra-angle handpiece or three-way syringe is provided to a medical unit-chair on which a patient sits or lies. Particularly, a dental unit-chair also has an oral washstand on which a patient can gargle with the water provided from a compressed water supply system.

According to the conventional art, the compressed water is provided by a compressor supplying compressed air. In other words, in the compressed water supply system a given amount of water is held in a storage tank and a part of the compressed air jet out from the compressor is supplied to the storage tank's upper portion. The water in the storage tank is jet out by a given level of pressure of the compressed air.

According to the conventional compressed water supply system, since the water in the storage tank becomes compressed water by the compressed air, if the water in the storage tank is all consumed, the compressed water can be supplied by refilling the storage tank, and the compressor should be operated whenever using the compressed water, thus increasing the power consumption, damaging the components, and reducing the life of the compressor.

In addition, the supply of the compressed water may be cut off during treatment, and in this occasion, the trouble is that the treatment cannot be restarted until the water fills in the storage tank. Since the compressed air is provided to the storage tank without using any air purifying device, the water and the air may be polluted with germs, and a portion to be treated may be infected. Even if the purified water is used, the dust in the air contaminates the water in the storage tank, thus propagating the germs enormously.

When using the water not purified as the compressed water, the dust and dirt in the water may be inserted into a small gap of the precise medical instrument such as the contra-angle handpiece, which damages the medical instrument and increases the consumption of components. If the dust and dirt cause damage to the medical instrument during treatment, the treatment cannot be restarted until the instrument is repaired.

In addition, since the temperature of the water provided to the oral washstand for the dental unit-chair is low, a patient may feel very chilly during gargling after treatment. Therefore, there is a conventional art with a small heater provided to a compressed water supply tube connecting the compressed water supply system to the oral washstand, thus supplying the hot water. However, it takes time to heat the water passing the compressed water supply tube.

SUMMARY OF THE INVENTION

Accordingly, the present invention is directed to a compressed water supply system for a dental unit-chair and a compressed water supply device that substantially obviate one or more of the problems due to limitations and disadvantages of the related art.

An object of the present invention is to provide a compressed water supply system for a dental unit-chair and a compressed water supply device which purify and continuously supply input water to which a given pressure is applied to a medical instrument on the dental unit-chair.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the present invention provides a compressed water supply system for a dental unit-chair including a water purifier purifying or sterilizing water from a water supply source, and supplying the water to which a given pressure is applied to a medical instrument installed on the dental unit-chair. The water purifier is designed to be of multi-stage to remove various alien substances, heavy metals, ions, germs, etc. from the compressed water, and is connected to at least one carbon filter or reverse osmotic pressure filter. The pressure means pressurizes the water from the water supply source and supplies the water to the water purifier under a given pressure used in the medical instrument on the dental unit-chair. A pump is used as the pressure means.

The compressed water supply system further includes a preliminary filter removing sands, floating materials, or rusty remainders from the water introduced to the pressure means; a storage tank storing the compressed water from the water purifier under a given pressure; a pressure control means installed between the water purifier and the storage tank; and a heating means heating the compressed water from the water purifier at a given temperature, and supplying the water to the medical instrument.

The compressed water supply system further includes an auxiliary filter removing an offensive taste, odor, coloring matters, ions, etc. from the compressed water that has passed the water purifier, and providing the drinking water and distilled water.

According to another aspect of the present invention, a compressed water supply device for a dental unit-chair includes a case; an inflow tube provided to the case and connected to a water supply source; a pump installed within the case and connected to the inflow tube to jet out the water from the water supply source under a given pressure; a water purifier provided to the case in multi-stage and removing various alien substances, chemical substances, heavy metals, ions, germs, etc. from the water supplied from the pump; and a compressed water supply tube provided to the case, connected with the water purifier, and connected to a medical instrument installed on the dental unit-chair, thus providing the compressed water thereto.

The inflow tube has a preliminary filter for removing sands, floating materials, or rusty remainders from the water. The water purifier includes at least one carbon filter removing chemical substances and the like from the compressed water jet out from the pump; and at least one reverse osmotic pressure filter connected to a waste water tube and removing heavy metals, ions or germs from the compressed water that has passed the carbon filter. A pressure gauge is installed between the carbon filter and the reverse osmotic pressure filter of the water purifier for measuring the pressure of the water compressed via the pump.

The compressed water supply device further includes a drinking water supply tube diverging from the compressed water supply tube and provided to the case; and an auxiliary filter provided to the drinking water supply tube and removing an offensive taste, odor, coloring matters, ions, etc. from the compressed water to supply the compressed water as drinking water and distilled water for disinfection.

The compressed water supply device further includes a storage tank storing the compressed water from the water purifier under a given pressure; a pressure control means installed between the water purifier and the storage tank; and a heating means heating the compressed water from the water purifier at a given temperature and supplying the water to the medical instrument.

The storage tank has a rubber bag having an elasticity and holding the compressed water under a given pressure. The heating means includes a heating tank to which the compressed water from the water purifier is introduced; an electric heater provided to the heating tank and heating the compressed water at a given temperature; a temperature sensor provided to the heating tank and measuring the temperature of the compressed water; a cutoff turning off the power of the electric heater if the heating tank is overheated; a fan cooling the air inside the case; and a disinfector sterilizing the compressed water held in the heating tank.

The compressed water supply device further includes an innoxious medical hose provided to the case and supplying the compressed water from the water purifier and the heating means to the medical instrument on the dental unit-chair.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the drawings:

In the drawings:

FIG. 1 is a block diagram schematically showing a compressed water supply system for a dental unit-chair in accordance with a first preferred embodiment of the present invention;

FIG. 2 is a block diagram schematically showing a compressed water supply system for a dental unit-chair in accordance with another preferred embodiment of the present invention;

FIG. 3 is a perspective view of a compressed water supply device for a dental unit-chair in accordance with another preferred embodiment of the present invention;

FIG. 4 is a partially-sectional perspective view of the compressed water supply device for a dental unit-chair in accordance with the first preferred embodiment of the present invention; and FIG. 5 is a rear-perspective view of the compressed water supply device for a dental unit-chair in accordance with the first preferred embodiment of the present invention.

DETAILED DESCRIPTION OF PREFERRED EMBODIMENT

Reference will now be made in detail to the preferred embodiments of the present invention, examples of which are illustrated in the accompanying drawings.

As shown in FIG. 1, the inventive compressed water supply system includes a water purifier purifying and sterilizing water from a water supply source 2, and providing the water to a medical instrument 4 installed on a dental unit-chair at a given pressure. The medical instrument 4 includes a contra-angle handpiece, a finishing bur or a three-way syringe. The water purifier is formed of multistages to remove various alien substances, heavy metals, ions, germs, etc. contained in the water from the water supply source 2, and includes at least one carbon filter 22 or reverse osmotic pressure filter 24. A first preferred embodiment of the compressed water supply system for a dental unit-chair further includes a pressure means that applies pressure to the water supplied when the pressure of the water from the water supply source 2 is lower than the pressure used by the medical instrument 4 installed on the dental unit-chair.

A pump 10 serves as the pressure means, and the pump 10's intake is connected to either a water pipe, the water supply source 2, or a water tank or underground water pipe, thus drawing in the water. The pressure of the compressed water from the pump 10 passes the carbon filters 22, 23 or reverse osmotic pressure filter 24, and the level of pressure applied to the medical instrument 4 is preset as a reference pressure in consideration of the loss of pressure that occurs in this process.

The pressure of the compressed water from the pump 10 is preset to keep the pressure of the compressed water supplied to the medical instrument 4 to be the same as that of the compressed air (about 2 to 4 $kgf/cm^2$) supplied to the contra-angle handpiece or three-way syringe that is installed on the dental unit-chair.

Another preferred embodiment of the compressed water supply system for a dental unit-chair, as shown in FIG. 2, further includes a preliminary filter for removing sands, floating materials, rusty remainders, etc. from the water introduced to the pump 10 from the water supply source 2, a storage tank 30 storing the compressed water that has passed the reverse osmotic pressure filter 24 of the water purifier under a given pressure, and a heating means heating the compressed water to a given temperature and supplying the water to the medical instrument 4. The preliminary filter includes a sediment filter 27, and an electric heater 44 serves as the heating means.

Still another preferred embodiment of the compressed water supply system for a dental unit-chair according to the present invention further includes a pressure control device 90 that is interposed between the water purifier and the storage tank 30 and controls the pressure of the compressed water from the storage tank 30, regularly.

The pressure control means 90 is designed to operate the pump 10 when the pressure of the compressed water from the storage tank 30 is lower than the reference pressure.

Still another preferred embodiment of the compressed water supply system for a dental unit-chair according to the present invention further includes an auxiliary filtering means that removes an offensive taste, a bad smell, coloring matters, etc. from the compressed water that has passed the reverse osmotic pressure filter 24.

The auxiliary filtering means includes a T.O.R. (taste odor remove) filter 29, a carbon filter.

As shown in FIGS. 3 to 5, a first preferred embodiment of the compressed water supply device for a dental unit-chair according to the present invention includes a case 50, an inflow tube 60 installed in the case 50 and connected to the water supply source 2, the pump 10 installed within the case 50 to be connected to the inflow tube 60 and jet out the water from the water supply source 2 by a given pressure, a water purifier 20 installed to be of multi-stage within the case 50 and removing various alien substances, chemical materials, heavy metals, ions, germs, etc. from the compressed water jet out from the pump 10, and a compressed water supply tube 62 connected with the water purifier 20 and installed on the case 50 to be connected to the medical instrument 4.

The inflow tube 60 has the preliminary filter 26 for removing the sands or floating materials from the compressed water. A sediment filter is used as this preliminary filter 26. Preferably, the preliminary filter 26's case is formed to be transparent so that a user can easily see from the outside the time to replace the used filter with new one.

The water purifier 20 includes the carbon filters 22, 23 for removing chemical materials from the compressed water jet out from the pump 10, and the reverse osmotic pressure filter 24 for removing heavy metals, ions, germs, etc. from the compressed water that has passed the carbon filters 22, 23. The reverse osmotic pressure filter 24 is connected with a waste water tube 68 for discharging removed materials. Various filters used for purifying the water may serve as the water purifier 20.

A pressure gauge 70 is interposed between the carbon filter 23 and the reverse osmotic pressure filter 24 of the water purifier 20 in order to measure the pressure of the compressed water from the pump 10.

The first preferred embodiment of the compressed water supply device for a dental unit-chair according to the present invention further includes a drinking water supply tube 64 divided from the compressed water supply tube 62 and installed in the case 10, and an auxiliary filter 28 provided to the drinking water supply tube 64, and removing offensive taste, bad smell, coloring matters, ions, etc. from the compressed water in order to supply the drinking water and distilled water for disinfection. A T.O.R. filter serves as the auxiliary filter 28.

The first preferred embodiment of the compressed water supply device for a dental unit-chair further includes the storage tank 30 holding the compressed water that has passed the reverse osmotic pressure filter 24 of the water purifier 20 under a given pressure, and a heating means 40 that heats the compressed water from the reverse osmotic pressure filter 24 to a given temperature and provides that water to the medical instrument 4.

The pressure control means 90 is interposed between the storage tank 30 and the reverse osmotic pressure filter 24 of the water purifier 20 so as to operate the pump 10 when the pressure of the compressed water from the storage tank 30 is lower than a given pressure.

The pressure control means 90 includes a pressure switch that can set a pressure to a given range. When the pressure of the compressed water is lower than the preset minimum pressure, the pressure control means 90 operates the pump 10, and when it is lower than the preset minimum pressure, the means 90 stops the pump 10. The storage tank 30 includes a storage chamber 32 holding the compressed water under a given pressure (about 2 to 4 kgf/cm$^2$) and a pressure chamber 34 that applies a given pressure to the chamber 32.

The pressure chamber 34 is filled with the air to which a given pressure is applied, and the storage chamber 32 and the pressure chamber 34 are designed to be relatively changed in volume. That is, the storage chamber 32 can be made of a rubber bag 36 with a given elasticity, and a pressure plate, pressurized by the compressed air, may be movably installed to divide the storage chamber 32 from the pressure chamber 34. If the compressed water from the pump 10 keeps on flowing to the storage chamber 32 in the storage tank 30's rubber bag 36 through the reverse osmotic pressure filter 24 of the water purifier 20, the storage chamber 32's pressure becomes higher than that of the pressure chamber 34. Thus, the storage chamber 32 becomes large in volume, and the pressure chamber 34 becomes relatively small in volume.

When the pressure in the storage chamber 32 is higher than the maximum pressure set in the pressure control means 90 by the compressed water continuously flowing thereto, the pressure control means 90 stops the pump 10.

If the medical instrument 4 mounted on the dental unit-chair is used under the above condition, the compressed water held in the storage tank 30's storage chamber 32 is supplied, and the rubber bag 36 deflates till the storage chamber 32 and the pressure chamber 34 are well-balanced in pressure level, so that the pressure chamber 34 becomes large in volume and the storage chamber 32 becomes relatively small in volume.

If the storage chamber 32's pressure becomes lower than the minimum pressure set in the pressure control means 90 as the compressed water is continuously discharged, the pressure control means 90 operates the pump 10.

The compressed water is either stored in or output from the storage tank in response to the pressure of each of the pressure chamber 34 and the storage chamber 32, which results from a difference between the pressure of the compressed water, supplied by the pump 10, and the pressure in the pressure chamber 34.

If the pressure in the storage tank 30 is large, i.e. the tank 30 is filled with the water, the compressed water is supplied under a pressure that is constant all the time by the pressure in the chamber 32 even though the pump 10 does not operate. If the pressure becomes small, i.e. the water in the tank 30 becomes decreased, the pressure control means 90 operates the pump 10 so that the compressed water can be continuously supplied under a pressure that is always constant.

The compressed water supply tube 62, connecting the water purifier 20 to the medical instrument 4, includes a purified water tube 66 connecting the reverse osmotic pressure filter 24 to the storage tank 30. A pressure gauge 72 for measuring the pressure of the compressed water that has passed the reverse osmotic pressure filter 24 is provided to the purified water tube 66. The pressure control means 90 is provided to the purified water tube 66. The auxiliary filter 28 provided to the drinking water supply tube 64 is connected to a drinking water branch tube 65 that diverges from the tube 66.

The heating means 40 includes a heating tank 42 to which the compressed water from the filter 24 of the purifier flows, and an electric heater 44 that is installed to surround the heating tank 42. Preferably, the heating tank 42 is covered with a heat-insulating material to prevent heat loss, and a temperature sensor 78 to measure the temperature of the compressed water in the tank 42. A temperature display 53 that indicates the temperature of the compressed water measured by the sensor 78 is provided to the case 50.

The tank 42 has a disinfector 38 that kills germs in the compressed water. The disinfector 38 kills germs by using ultraviolet rays or ozone. An ultraviolet lamp or ozone apparatus may serve as the disinfector 38. A compressed water branch tube 67 diverging from the tube 66 and the compressed water supply tube 62 are connected to the heating tank 42.

The compressed water flows to the tank 42 through the purified water tube 66 and the compressed water branch tube 67, and heated by the electric heater 44 to be supplied to the medical instrument 4 through the compressed water supply tube 62. The compressed water supply tube 62 is connected to an innoxious medical hose (not illustrated) that is provided to the case 50 and supplies the compressed water that has passed the water purifier and the heating means 40 to the medical instrument 4.

The heating means 40 further includes a cutoff 80 and a fan 46 to prevent the tank 42 from being overheated. The fan 46 is provided to the case 50, and an intake 58 is formed on the case 50 to inhale the air from the outside. The case 50 also has a wire 56 with a plug and a power cutoff 57 for breaking the power if a short circuit or overload occurs.

A door 51 is provided to the back of the case 50 and can be opened or closed for repairs.

It is preferable that the compressed water supply device according to the first preferred embodiment of the present invention has a controller (not shown) to automatically control the electric heater 44 of the heating means 40, the fan 46, and the pump 10 in a preset range.

The controller may be designed to compare the pressure, measured by each of the pressure gauges 70, 72, to the preset pressure, thus automatically controlling the pump 10 in response to the comparison's result. In addition, the controller may be designed to compare the temperature of the temperature sensor 78 to the preset temperature, thereby automatically controlling the electric heater 44 and the fan 46 in response to the comparison's result.

In the first preferred embodiment of the present invention, a spare water supply tube (not shown) may be formed to diverge from the tube 60 through a three-way valve so as to directly provide the water from the water supply source 2 to the medical instrument 4 if the pump 10 or the water purifier 20 is out of order not to supply the compressed water.

The following description concerns the operation of the inventive compressed water supply device for a dental unit-chair.

The inflow tube 60 is connected to a water pipe, the water supply source 2, and the compressed water supply tube 62, the waste water tube 68, and the drinking water supply tube 64 are then respectively connected to the medical instrument 4, a drain, and a drinking waterstand installed in a waiting room.

Once a power switch 14 is turned on under this condition, the pump 10 draws in the water from the water supply source 2, and then jets out the water under a given pressure.

As the water drawn by the pump 10 passes the preliminary filter 26, sands, floating materials or rusty remainders are removed from that water. As the compressed water from the pump 10 passes the carbon filters 22, 23 of the water purifier 20, chemical substances are removed from the water, and heavy metals or germs are removed from the water through the reverse osmotic pressure filter 24. The water is then introduced to the heating tank 42 of the heating means 40 through the purified water tube 66 and the compressed water branch tube 67.

The compressed water flowing to the heating tank 42 is heated by the electric heater 44, and then supplied to the medical instrument 4 through the compressed water supply tube 62. The heated compressed water supplied through the compressed water supply tube 62 is used for gargling on the oral washstand. The remaining compressed water that is not supplied to the medical instrument 4 flows to the tank 30 through the purified water tube 66 until the pressure in the storage chamber 32 reaches to a given level (e.g. a maximum pressure set in the pressure control means 90).

A part of the compressed water provided through the tube 66 is supplied to the auxiliary filter 28, passing the drinking water branch tube 65, and the water from which offensive taste and odor are removed via the auxiliary filter 28 is provided to the drinking waterstand installed in the waiting room.

If the compressed water is not used in the medical instrument 4 or drinking waterstand, the water from the pump 10 continuously flows in until the storage chamber 32 and the pressure chamber 34 are well-balanced in pressure or the pressure reaches to the maximum level set in the pressure control means 90. Once the pressure balance is realized and the pressure goes to the maximum point, the pump 10 stops.

Once the medical instrument 4 is operated or the oral washstand is used under this condition, the storage tank 30's compressed water is output through the purified water tube 66, and supplied via the heating tank 42 and the compressed water supply tube 62. When using the drinking waterstand, the compressed water in the tank 30 is output through the purified water tube 66 and supplied via the drinking water branch tube 65, the auxiliary filter 28, and the drinking water supply tube 64.

The force flowing out the compressed water from the tank 30 consists of the pressure in the pressure chamber 34 and the rubber bag 36's elasticity.

If the pressure in the storage chamber 32 is smaller than the minimum pressure as the compressed water is output from the storage tank 30, the pressure control device 90 operates the pump 10, and the pump 10 draws in the water from the water supply source 2, thus repeating the above steps.

In the above preferred embodiments, the compressed water supply system and the compressed water supply device for a dental unit-chair are applied to a dental equipment, and the present invention is not limited thereto and applicable to various medical instruments needing the compressed water.

As described above, in the inventive compressed water supply system and the compressed water supply device for a dental unit-chair, a given pressure is applied to the water from the water supply source, and the compressed water is then purified via the multi-stage water purifier to be provided to various medical equipments. Therefore, with the excellent sanitary conditions of the compressed water, the medical equipments are not damaged by dirt, dust or harmful substances in the water, and the compressed water can be automatically supplied.

In addition, the purified water of the present invention may be used as drinking water or for gargling after dental treatment. When using a small amount of the compressed water, the compressed water in the storage tank is supplied and used hereby preventing the pressure means or pump from temporarily operating and enhancing the durability.

It will be apparent to those skilled in the art that various modifications and variations can be made in the compressed water supply system and the compressed water supply device of the present invention without departing from the spirit or scope of the invention. Thus, it is intended that the present invention cover the modifications and variations of this invention provided they come within the scope of the appended claims and their equivalents.

What is claimed is:

1. Apparatus for supplying pressurized water to a dental instrument and pressurized, purified water to an associated drinking water basin, comprising:

an inlet line adapted for connection to a water supply source to receive inlet water therefrom, a preliminary filter means connected to said inlet line, a pump for pressurizing the inlet water after passage through the preliminary filter means, a further filter means connected to said pump, said further filter means including a carbon filter and a reverse osmotic filter, a connecting line between said further filter means and an auxiliary filter, said auxiliary filter having an outlet connected to said drinking water basin, a further line connect to said connecting line at a location between said further filter means and said auxiliary filter, an electric heater connected by a branch line to said further line for heating pressurized water therein, said heater having an outlet connected to said dental instrument for supplying heated pressurized water thereto, a pressure control means in said further line downstream of said branch line, and a storage tank connected to said pressure control means for storing pressurized water and maintaining the water above a specific minimum pressure, said storage tank being connected to deactivate said pump when a given maximum pressure is reached in said storage tank, said storage tank supplying pressurized water therein to said drinking water basin and to said heater, when said pump is deactivated and until said minimum pressure is reached whereupon said pump is re-activated.

2. Apparatus for supplying pressurized, heated water to a dental instrument and pressurized purified drinking water to an associated drinking water basin comprising:

a casing having an inlet connection for receiving supply water, a first outlet connection to supply pressurized, heated water to said dental instrument, and a second outlet connection to supply purified drinking water to said water basin, a preliminary filter means connected to said inlet connection for filtering said supply water at said inlet connection, a pump connected to said preliminary filtering means for pressurizing the inlet water after passage through the preliminary filtering means, a further filtering means connected to said pump, a connection line connecting said further filter means and an auxiliary filter, said auxiliary filter being connected to said second outlet connection for supplying pressurized, filtered water thereto, a further line connected to said connecting line at a location between said further filter means and said auxiliary filter, an electric heater connected by a branch line to said further line for heating pressurized water therein, said heater having an outlet connected to said first outlet for supplying heated pressurized water to said dental instrument, a pressure control means in said further line downstream of said branch line, and a storage tank connected to said pressure control means for storing pressurized water therefrom and maintaining the water above a specific minimum pressure, said storage tank being connected to deactivate said pump when a given maximum pressure is reached in said storage tank, said storage tank supplying pressurized water therein to said drinking water basin and to said heater when said pump is deactivated and until said minimum pressure is reached whereupon said pump is re-activated, said casing containing said preliminary filter means, said pump, said further filtering means, said auxiliary filter, said heater and said storage tank.

3. Apparatus as claimed in claim 2, wherein said further filtering means comprises a carbon filter and a reverse osmotic filter connected in sequence.

4. Apparatus as claimed in claim 3, comprising a waste water tube connected to said reverse osmotic filter for discharging separated waste water to a waste water outlet on said casing.

5. Apparatus as claimed in claim 2, comprising a pressure gauge connected between said carbon filter and said reverse osmotic filter.

6. Apparatus as claimed in claim 2, wherein said storage tank includes a flexible bag containing the pressurized water at a pressure between said maximum and minimum pressures.

7. Apparatus as claimed in claim 2, wherein said heater comprises a heating tank containing pressurized water, an electric heating element connected to said tank to heat the water therein, a temperature sensor for sensing temperature of the water in said heating tank and switch means for interrupting power supply to said heating element when the water temperature in said tank reaches a predetermined value, said apparatus further comprising a cooling fan in said casing.

8. Apparatus as claimed in claim 7, comprising a disinfector in said heating tank.

* * * * *